United States Patent [19]

Akutsu et al.

[11] Patent Number: 4,839,443
[45] Date of Patent: Jun. 13, 1989

[54] POLYSILOXANE CONTAINING HYDROXYL GROUPS AND A SILICONE-MODIFIED POLYURETHANE USING THE SAME

[75] Inventors: Yoshinori Akutsu, Kawasakishi; Takaharu Nakano, Yokohamashi; Takahiro Saho, Yokohamashi; Nobumasa Ohtake, Yokohamashi; Hirofumi Yasuda, Yokohamashi; Tamio Kimura, Yokohamashi, all of Japan

[73] Assignee: Chisso Corporation, Osaka, Japan

[21] Appl. No.: 143,746

[22] Filed: Jan. 14, 1988

[30] Foreign Application Priority Data

Feb. 4, 1987 [JP] Japan .................. 62-23888
May 22, 1987 [JP] Japan .................. 62-125177

[51] Int. Cl.$^4$ .......................... C08F 283/00
[52] U.S. Cl. ......................... 525/474; 556/445; 556/449; 556/450; 556/453; 556/456; 528/31; 528/32; 528/25; 528/26; 528/27; 528/28; 528/15
[58] Field of Search ............... 556/445, 449, 450, 453, 556/456; 528/31, 15, 32, 25, 26, 27, 28; 525/474

[56] References Cited

U.S. PATENT DOCUMENTS

3,381,019 4/1968 Morehouse .................. 556/445

Primary Examiner—Melvyn I. Marquis
Attorney, Agent, or Firm—Fred Philpitt

[57] ABSTRACT

A polysiloxane compound modified with two hydroxyl groups at the one end thereof and particularly suitable for improving the surface characteristics of resins prepared by polycondensation of a polyol with another polyfunctional compound, and a silicone-modified polyurethane having superior characteristics such as low frictional properties, water repellency, oil repellency, thrombosis resistance, etc. and also a process for producing the polyurethane are provided, which polysiloxane compound expressed by the formula

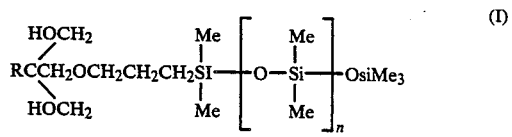

wherein R represents H, Me (methyl) or Et (ethyl) and n represents an integer of 0 to 4,000, and which silicone-modified polyurethane is obtained from a compound having at least two isocyanate groups and a compound having at least two hydroxyl groups, and by using as a part of the compound having at least two hydroxyl groups, the polysiloxane compound of the above formula (I) in the urethane bond-forming reaction.

2 Claims, No Drawings

POLYSILOXANE CONTAINING HYDROXYL GROUPS AND A SILICONE-MODIFIED POLYURETHANE USING THE SAME

BACKGROUND OF THE INVENTION

1. Field of the Invention

The present invention in the first aspect relates to a silicon compound used for modifying the surface of synthetic resins, and more particularly it relates to a novel organosilicon compound useful for improving the surface characteristics of synthetic high-molecular resins, having applied the reactivity of polyols.

The present invention in the second aspect relates to a silicone-modified polyurethane using the above-mentioned organosilicon compound and a process for producing the same.

2. Description of the Related Art

For the purpose of imparting the unique surface characteristics of polysiloxane compounds such as water repellency, non-adhesive characteristics, stain resistance, etc. to synthetic resins, silicone oils, etc. have been used by blending them with various synthetic resins or chemically bonding them thereto.

Namely, in the case of a mere blend, there is a drawback that a bleeding phenomenon is liable to occur due to the inferior compatibility of silicone resins with various synthetic resins; hence in order to overcome the drawback, for example, modification has been carried out using a siloxane compound having a vinyl-polymerizable double bond (Japanese patent application laid-open No. Sho 59-78236/1984). Polymers such as polyurethanes, polyesters, etc. obtained by reacting a polyol with a compound having a plurality of reactive groups reactive with the reactive hydroxyl groups of the polyol cannot be subjected to silicone-modification with some siloxane compounds having a vinyl-polymerizable double bond; hence for such polymers, polysiloxanes modified with hydroxyl groups at both the ends thereof have so far been used. However, when such polysiloxanes modified with hydroxyl groups at both the ends thereof are used, there is a drawback that since the polysiloxane chain is incorporated into the main chain of a polymer to be modified, it is necessary to increase the proportion of the polysiloxane compound required for improving the surface characteristics of molded products of resins using the polymer, relative to the polymer.

In order to overcome the drawback, the present inventors have provided a polysiloxane compound modified with two hydroxyl groups at the one end thereof, as a compound preferred for silicone-modifying a polymer prepared by reacting a polyol with a compound having a plurality of reactive groups reactive with the reactive hydroxyl group of the polyol (Japanese patent application No. Sho 61-38765/1986). However, the two hydroxyl groups of this polysiloxane compound modified with two hydroxyl groups at the one end thereof are different in the reativity; hence there has been a fear that when this polysiloxane modified with two hydroxyl group at the one end thereof is introduced into synthetic resins such as polyurethanes or polyesters in order to modify the synthetic resins, then only one hydroxyl group thereof reacts preferentially and hence the surface characteristics expected for the resulting molded products of resins are not developed.

As apparent from the foregoing, the object of the present invention in the first aspect is to provide a polysiloxane compound modified with two hydroxyl groups at the one end thereof which is particularly superior for improving the surface characteristics of resins prepared from a polymer formed by polycondensation of a polyol with another polyfunctional compound.

Next, the related art relative to the present invention in the second aspect will be described.

In order to impart water repellency, oil repellency, low frictional properties or thrombosis resistance to polyurethanes, a process of modifying polyurethanes with polydiorganosiloxanes has so far been carried out. Polydiorganosiloxanes are intrinsically a polymer having an inferior compatibility with polyurethanes; hence a mere blending process in a process for imparting the above-mentioned various characteristics of polydiorganosiloxanes to polyurethanes cannot be employed due to a bleeding phenomenon of polydiorganosiloxanes onto the surface of the resulting blend. Thus, various attempts have been made such as ① a process of using a polydiorganosiloxane having silanol group, alcohol group or isocyanate group at both the ends thereof and introducing the polydiorganosiloxane chain into the main chain of polyurethanes to prepare a block copolymer (e.g. Japanese patent application laid-open No. Sho 60-238315/1985);

② a process of using a polydiorganosiloxane having silanol group at the one end thereof and introducing the polydiorganosiloxane chain into the end of polyurethanes;

③ a process of using polydiorganosiloxane of addition reaction type and forming the so-called interdependently penetrating network structure (hereinafter abbreviated to "IPN") from a polyurethane and the polydiorganosiloxane (e.g. Japanese patent application laid-open No. Sho 58-189257/1983); etc.

However, according to these processes, (a) in the case of the block copolymer obtained by introducing the polydiorganosiloxane chain into the main chain of a polyurethane, reduction in the mechanical strength due to the polysiloxane chain occurs; in the case of the end-modified polymer obtained by introducing the polydiorganosiloxane chain into the end of a polyurethane, no sufficient improvement in the characteristics is obtained; further, (b) in the case of the process of forming IPN, since the compatibility of a polyurethane with the polydiorganosiloxane is poor, it is not easy to form IPN wherein the latter is uniformly dispersed in the former; hence apart from the reduction in the mechanical strength, unless the polydiorganosiloxane is used in a considerably large proportion, no sufficient improvement in the characteristics is obtained.

Further, in the case of a polyurethane obtained by using as a part of a hydroxyl groups-containing compound, a silicone compound disclosed in Japanese patent application No. Sho 61-67962/1986 invented by the present inventors and expressed by the formula (B)

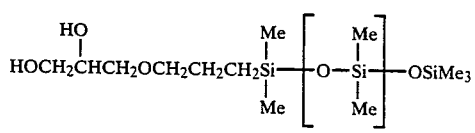

wherein Me represents methyl group and n represents an integer of 0 to 4,000, there is a problem that since the two hydroxyl groups of the hydroxyl groupcontaining compound are primary and secondary, respectively, the reactivities thereof are different so that it is difficult to obtain stabilized physical properties.

The present inventors have made extensive research in order to overcome the problems of the prior art and provide a polyurethane having preferred characteristics such as low frictional properties, water repellency, oil repellency, thrombosis resistance, etc.

As a result, we have found that when a polyisocyanate is reacted with a polyhydroxy compound according to a conventional process, if a part of the polyhydroxy compound is replaced by a silicone compound disclosed in Japanese patent application No. Sho 62-23888, i.e. a compound expressed by the formula (I)

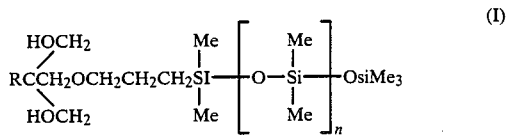

wherein R represents H, Me or Et, Me represents methyl group, Et represents ethyl group and n represents an integer of 0 to 4,000, to carry out the reaction, then a polyurethane having various superior physical properties as described above is obtained, and have completed the present invention.

As apparent from the foregoing, the object of the present invention in the second aspect is to provide a process for producing a polyurethane having various superior physical properties as described above.

SUMMARY OF THE INVENTION

The present invention in the first aspect resides in a polysiloxane compound modified with two hydroxyl groups at the one end thereof and expressed by the formula

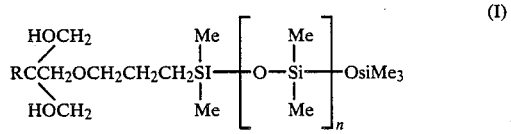

wherein R represents H, Me or Et, Me represents methyl group, Et represents ethyl group and n represents an integer of 0 to 4,000.

Further, the present invention in the second aspect resides in a silicone-modified polyurethane and a process for producing the same, characterized in that said polyurethane is obtained from a compound having at least two isocyanate groups and a compound having at least two hydroxyl groups, and in the reaction of forming urethane bond, a silicone compound expressed by the formula

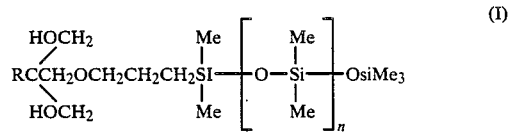

wherein R represents H, Me or Et, Me represents methyl group, Et represents ethyl group and n represents an integer of 0 to 4,000, is used as a part of said compound containing at least two hydroxyl groups.

DETAILED DESCRIPTION OF PREFERRED EMBODIMENTS

The polysiloxane compound, as apparent from the formula (I), is characterized by being chain-terminated with trimethylsilyl group at the one end thereof and substituted alkyl group having two primary hydroxyl groups at the other end thereof. "n" in the compound of the formula (I) has an upper limit of 4,000 in terms of the number average polymerization degree of the linear chain part of the polydimethylsiloxane. When the compound of the present invention is used for introducing the polydimethylsiloxane chain into a polymer obtained by polycondensation using a polyol as a one side monomer, such as polyurethanes, polyesters, etc., the n value of the compound of the formula (I) may be varied depending on the characteristics required for the objective polymers, but n may be usually preferred to be 1,000 or less in terms of number average polymerization degree, in other words, 80,000 or less in terms of a number average molecular weight.

Next, an embodiment of the process for producing the compound of the present invention will be described.

Firstly, a 2-(2-propenyloxy)methyl-2-alkylpropan-1,3-diol (II) is reacted with hexamethyldisilazane (III) in the presence of trimethylchlorosilane to prepare a 1,3-bis(trimethylsiloxy)-2-(2-propenyloxy)methyl-2-alkylpropane (IV), followed by reacting a polydimethylsiloxane compound modified with hydrogen at the one end thereof (hereinafter abbreviated to "modified with Si-H at the one end thereof) (V) with above (IV) in the presence of an addition reaction catalyst such as a platinum complex, etc. in an inert gas atmosphere to prepare a polydimethylsiloxane derivative of the formula (VI), and detrimethylsilylating the (VI) to obtain the objective polysiloxane compound modified with two hydroxyl groups at the one end thereof (I).

The foregoing is illustrated by the following reaction equation:

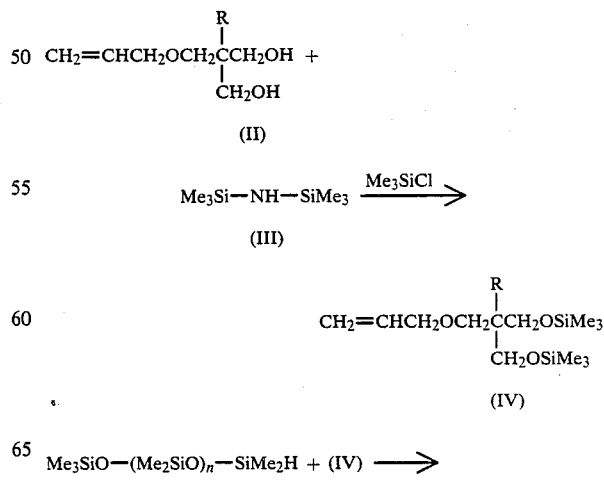

-continued

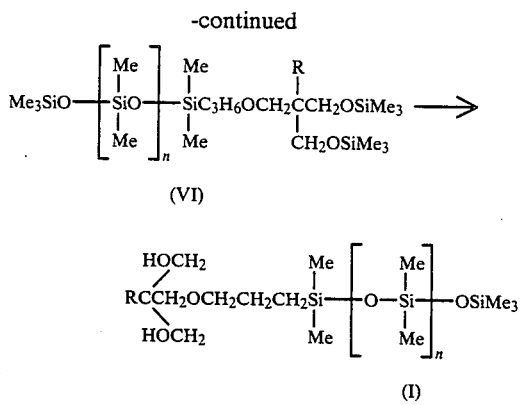

(VI)

$$\underset{HOCH_2}{\overset{HOCH_2}{>}}RCCH_2OCH_2CH_2CH_2Si\underset{Me}{\overset{Me}{|}}{-}\left[O-\underset{Me}{\overset{Me}{\underset{|}{Si}}}\right]_n-OSiMe_3$$

(I)

wherein R represents H, Me (methyl group) or Et (ethyl group).

As to a polydimethylsiloxane modified with Si-H at the one end thereof, having $n \geq 1$ in the formula (V), hexamethylcyclotrisiloxane is subjected to living polymerization with lithium trimethylsilanolate or sodium trimethylsilanolate, followed by using dimethylchlorosilane as a chian terminating agent to obtain a product having a desired average polymerization degree. The thus prepared polysiloxane modified with Si-H at the one end thereof is a product having an adjusted molecular weight and molecular weight distribution, and if the average molecular weight is 80,000 or less, it can be optionally prepared. Further, even a product having a larger average molecular weight than the above may be prepared by varying the conditions of living polymerization. Further, the compound of the formula (V) wherein n=0 is pentamethyldisiloxane and this is easily commercially available. In the reaction of the polydimethylsiloxane compound modified with Si-H at the one end thereof (V) with the propenyloxymethylalkylpropanediol derivative (IV), it is preferred to use the latter in an equimolecular quantity or more relative to that of the former, preferably 1.2 times equivalent or more relative thereto. As the catalyst for this hydrosilylation reaction, it is generally possible to use a complex compound of metal elements belonging to group VIII of the Periodic Table, and a solution of chloroplatinic acid dissolved in an alcohol or a carbonyl compound or a complex of various olefins with platinum or rhodium may be preferably used. The detrimethylsilylation reaction of the formula (VI) may be carried out using a lower alcohol such as methanol, ethanol, etc. or hydrochloric acid. When an alcohol is used, the detrimethylsilylation can be easily carried out by adding the alcohol to the polysiloxane of the formula (VI) and heating the mixture under reflux for several hours, and when hydrochloric acid is used, the detrimethylsilylation can be easily carried out by adding a suitable quantity of hydrochloric acid to the compound of the formula (VI) and agitating the mixture at room temperature for several hours.

When the compound of the present invention is used in place of the above-mentioned polysiloxane having hydroxyl groups of different reactivities at the one end thereof, as one of monomers for producing polyurethanes, polyesters, etc., there is obtained a polymer having a structure wherein the linear chain of the polydimethylsiloxane is incorporated as a branched chain by the medium of the two hydroxyl groups at the one end thereof into the main chain of the polymer. The resulting polymer has various functions such as water repellency, stain resistance, non-adhesive properties, attribution resistance, heat resistance, etc. as the surface characteristics of molded products obtained from the polymer, imparted by the siloxane compound of the present invention.

As apparent from Examples mentioned later, a novel siloxane compound modified with dihydroxyl group at the one end thereof is obtained according to the present invention.

As to the compounds having at least two isocyanate groups or the compounds having at least two hydroxyl groups, used in the present invention in the second aspect, any of compounds usable as raw materials for producing conventional polyurethanes may be used and have no particular limitation.

Namely, as the compounds having at least two isocyanate groups, examples of compounds which are basic raw materials for polyurethanes and usually referred to as diisocyanate are tolylene diisocyanate, diphenylmethane diisocyanate, dianisidine diisocyanate, diphenyl ether diisocyanate, bitolylene diisocyanate, naphthalene diisocyanate, hexamethylene diisocyanate, isophorone diisocyanate, lysine diisocyanate methyl ester, metaxylene diisocyanate, 2,2,4-trimethylhexamethylene diisocyanate, dimer acid diisocyanate, isopropylidene bis(4-cyclohexylisocyanate), cyclohexylmethane diisocyanate, methylcyclohexane diisocyanate, tolylene diisocyanate dimer, etc. Further, triphenylmethane triisocyanate, triisocyanate phenylthiophosphate or compounds having three or more cyanate groups such as adducts of the above-mentioned diisocyanates to polyols such as trimethylolpropane, trimethylolethane, trimethylolmethane, etc. may also be enumerated.

Besides, almost all of compounds having two or more cyanate groups such as prepolymers of these isocyanate-containing compounds with polyols or compounds containing two or more amino groups, which prepolymers contain two or more isocyanate groups, may be used. Further, products obtained by blocking these isocyanates with a compound having active hydrogen atom such as phenols, oximes, lactams, sodium hydrogen sulfate, etc. i.e. the so-called blocked isocyanates may also be used.

Further, examples of compounds having at least two hydroxyl groups, used in the present invention, are alkane diols such as ethylene glycol, propylene glycol, diethylene glycol, triethylene glycol, 1,3-butanediol, 1,4-butanediol, neopentyl glycol, 1,5-pentanediol, 2-methyl-2,4-pentanediol, 1,6-hexanediol, 2,5-hexanediol, etc., polyols having three or more hydroxyl groups such as glycerine, trimethylolpropane, trimethylolethane, trimethylolmethane, pentaerythritol, sorbitol, etc., polyoxyalkylene glycols such as polyethylene glycol, polypropylene glycol, polytetramethylene glyco, copolymer of polyethylene glycol with polypropylene glycol, etc., polyether polyols obtained from polyols such as glycerine or compounds having two or more amino groups and alkylene oxides, products obtained by reacting compounds containing hydroxyl groups, as illustrated above, with polybasic acids such as adipic acid, maleic anhydride, fumaric acid, succinic anhydride, itaconic acid, sebacic acid, phthalic anhydride, isophthalic acid, trimellitic acid, pyromellitic anhydride, etc., i.e. the so-called polyester polyols, polylactone ester polyol obtained by ring opening of $\epsilon$-caprolactam, etc.

In addition, naturally, in either cases of the above-mentioned isocyanate-containing compounds and hydroxyl group-containing compounds, even when two or more compounds are used with respect of the former compounds and the latter compounds, no problem is raised.

In general, polyurethanes are produced by suitably combining compounds having at least two isocyanates with compounds having at least two hydroxyl groups, adequately blending subsidiary raw materials such as urethanization reaction-promoting catalyst, foaming agent, pigment, curing agent (cross-linking agent), chain-lengthening agent, stabilizer, etc. and in some cases, using solvents, under various selected conditions such as reaction conditions, post-treatment conditions, etc., and have been broadly applied to elastomer, foam, paint and lacquer, adhesive, sealant, binder, elastic fiber, etc. With regard to the case where polyurethanes are applied to elastomer, as a representative example among the above-mentioned use applications, the process for producing silicone-modified polyurethane of the present invention in the second aspect will be described.

In addition, as to the production process of polyurethanes, the process of reacting compounds containing isocyanate group with compounds containing hydroxyl group, basically includes a process of feeding the total raw materials at the same time and heating them to effect reaction in one step, and a process of converting either one or both of the compounds containing isocyanate group and the compounds containing hydroxyl group into prepolymer(s), followed by successively reacting the prepolymer(s) in two or more steps. In the present invention, either of the above-mentioned processes may be employed, and in the case of the one step reaction, the silicone compound (I) may be used as a part of the hydroxyl group-containing compounds as the raw material, and since the proportion by weight of the silicone compound contained in the resulting polyurethane is relatively small, no particular device is required for the reaction manner, but the compatibility of the silicone compound (I) with the resulting polyurethane is inferior; hence it is preferred to use a solvent for uniform reaction.

Further, in the case where a prepolymer is first prepared, followed by successive reactions, even when a compound having at least two isocyanate groups is used in excess of the silicone compound (I) for preparing a prepolymer of an end isocyanate type, the proportion by weight of the silicone compound (I) is considerably large; hence use of a solvent is indispensable for effecting uniform and complete reaction.

Examples of solvents which are inert to the isocyanate group and soluble in the resulting polyurethane are aromatic halides such as monochlorobenzene, dichlorobenzene, etc., esters such as 1,3-dimethylisobutyl acetate, 3-methoxybutyl acetate, etc., ketones such as methyl isobutyl ketone, cyclohexanone, etc., ethers such as dibutyl ether, dioxane, anisole, methoxytoluene, propylene glycol dimethyl ether, diethylene glycol dimethyl ether, etc.

When a compound having at least two isocyanate groups is used in excess of the silicone compound (I) in the presence of a solvent as described above to prepare a prepolymer of isocyanate type, the two compounds are reacted on heating at a temperature of 50° C. or higher, in a molar ratio of the isocyanate group-containing compound to the silicone compound (I) of 1.2 or more.

Further, as to the thus obtained prepolymer solution, the solvent is distilled off from the solution, followed by using the resulting material as a part of the compound having at least two isocyanate groups and reacting it with the so-called polyol compound having at least two hydroxyl groups, whereby it is possible to produce a silicone-modified polyurethane. Alternatively, the prepolymer solution is reacted with a separately prepared urethane polymer of polyol type without distilling off the solvent, followed by distilling off the solvent, whereby it is also possible to prepare a silicone-modified polyurethane.

The thus obtained silicone-modified polyurethane may be used as a modifier by reacting with another polyurethane not modified with a silicone for example according to co-addition polymerization for example by means of an extruder, in the presence of a chainlengthening agent or cross-linking agent such as diisocyanate compound, triisocyanate compound, dihydroxy compound, polyol, diamine, water, etc.

In addition, in the polyurethane formation reaction, particularly the chain-lengthening reaction using a prepolymer or the co-addition polymerization reaction of polyurethane with one another, conventionally used catalysts for promoting such reactions such as acid catalysts e.g. inorganic acids, phosphoric acid or boric acid ester, p-toluenesulfonic acid, amine catalysts e.g. N-methylmorpholine, triethylamine, N,N-dimethylbenzylamine, N,N'-dimethylpiperazine, triethylenediamine, N,N,N',N'-tetramethylethylenediamine, N,N,N',N'-tetramethylhexamethylenediamine, N,N,N',N'',N''-pentamethyldiethylenetriamine, hexamethylenetetramine, etc., metal catalysts e.g. cobalt naphthenate, lead naphthenate, zinc naphthenate, titanous chloride, titanic chloride, tri-n-butyltin acetate, trimethyltin hydroxide, dimethyltin dichloride, dibutyltin dilaurate, titanous octylate, tetraoctyl titanate, cobalt octylate, antimony trichloride, etc., may also be used in the present invention.

As described above in detail, the silicone-modified polyurethane of the present invention in the second aspect uses a polydiorganosiloxane hindered at the one end thereof with an organic group having two hydroxyl groups to thereby form a structure wherein the polydiorganosiloxane chain is branched on the side chain of a polyurethane; thus differently from the case where a polydiorganosiloxane chain is introduced into the main chain of a polyurethane to form a block copolymer, it has become possible to impart characteristics based on the polydiorganosiloxane chain such as low frictional properties, water repellency, oil repellency, thrombosis resistance, etc. without reducing the mechanical strength intrinsic of polyurethane. Further, in this case, the following is anticipated:

since the polydiorganosiloxane chain branched on the side chain has trimethylsiloxane group at the other end thereof and has no reactivity, its movement is not restricted and also since its compatibility with the main chain polyurethane is poor, it tends to go away from the main chain.

As to this function, when the silicone-modified polyurethane of the present invention as it is or blended with a resin such as polyurethane homopolymer is used for molded products, film, coating or binder, the above-mentioned function might be considered to cause a relief phenomenon of the polydiorganosiloxane on the surface of the molded products, etc. as in the case of a mere polymer blend, but since the product of the present invention is chemically bonded onto the main chain, it is not freed in the form of the polydiorganosiloxane and there occurs no sticky phenomenon.

Due to such an effectiveness, when the siliconemodified polyurethane of the present invention is used as a modifier, even if the quantity of the polydiorganosiloxane hindered with an organic group having two hydroxyl groups at the one end thereof is small, a product having not only low frictional properties i.e. surface slip characteristics, but also preferred characteristics of the polydiorganosiloxane imparted fully is obtained.

Further, since the silicone-modified polyurethane of the present invention has preferred characteristics as described, it can be advantageously used not only as belt for belt conveyer, but also as a material for molded products needing low frictional properties, as a component of coating for release paper, as a coating needing water repellency or oil repellency, as a binder for magnetic tape, as a component of coating for back coat, or as a molding material used in the medical field where thrombosis resistance is required.

The present invention will be described in more detail by way of Examples, but it should not be construed to be limited thereto.

EXAMPLE 1

2-(3'-pentamethyldisiloxanylpropyloxy)methyl-2-methylpropan-1,3-diol

A solution (4 μl) of chloroplatinic acid (1 g) dissolved in isopropanol (20 ml) and 1,3-bis(trimethylsilyloxy)-2(2-propenyloxy)methyl-2-methylpropane (1.0 g, 3.3 mmols) were heated with stirring in a flask in nitrogen atmosphere, followed by dropwise dropping pentamethyldisiloxane (0.73 g, 4.8 mmols) at 80° C., further agitating the mixture for 2 hours at 80° C., and distilling the reaction mixture to obtain a fraction of a b.p. of 150° C./10 mmHg (colorless, transparent liquid, 1.19 g, yield 80%).

the results of $^1$H-NMR, IR and mass spectra of this product are described below and the product was confirmed to be a siloxane compound having the following structural formula:

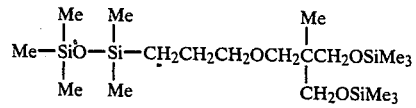

$^1$H—NMR (CDCl$_3$): δ (ppm)
  0.06(Si—Me$_3$, s, 33H)
  0.56(—CH$_2$—Si, m, 2H)
  0.86(CH$_3$—C≡, s, 3H)
  1.58(—CH$_2$—, m, 2H)
  3.17(—CH$_2$—, s, 2H)
  3.33(—CH$_2$—, t, 2H)
  3.40(—CH$_2$—, s, 4H)
IR (KBr) ν max
  2970 cm$^{-1}$ (C—H)
  1120~1050 cm$^{-1}$ (Si—O)
MS m/e: 452 (M$^+$)

Next, the thus obtained siloxane compound (1.0 g, 2.2 mmols) and methanol (40 ml) were fed into a flask, followed by heating the mixture with stirring for 2 hours and distilling the reaction mixture to obtain a fraction of a b.p. of 160° C./10 mmHg (colorless, transparent liquid 0.55 g, yield 80%). The analytical results of this liquid are shown below and the product was confirmed to be the objective siloxane compound having the following structural formula:

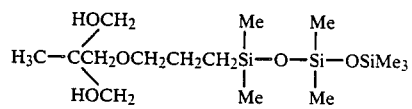

$^1$H—NMR (CDCl$_3$): δ (ppm)
  0.06(Si—Me$_3$, s, 33H)
  0.53(—CH$_2$—Si, m, 2H)
  0.83(CH$_3$—C≡, s, 3H)
  1.58(—CH$_2$—, m, 2H)
  3.10(C—OH, bs, 2H)
  3.37(—CH$_2$—, t, 2H)
  3.40(—CH$_2$—, s, 2H)
  3.63(—CH$_2$—, s, 4H)
IR (KBr) ν max
  3400 cm$^{-1}$ (O—H)
  2970 cm$^{-1}$ (C—H)
  1120~1050 cm$^{-1}$ (Si—O)
MS m/e: 308 (M$^+$)

EXAMPLE 2

A dimethylsiloxane oligomer modified with Si-H at the one end thereof (hydrogen equivalent 5,600; hence an oligomer having an average molecular weight of 5,600) (100 g, 0.018 mol) was used in place of pentamethyldisiloxane in Example 1 and it was reacted with 1,3-bis(trimethylsiloxy)-2-(2-propenyloxy)methyl-2-methylpropane (7.1 g, 23 mmols) in the same manner as in Example 1, followed by distilling off unreacted raw materials and low boiling fractions from the reaction mixture solution at 150° C./1 mmHg, cooling the distillation residual solution, adding methanol (100 ml) to the solution, refluxing the mixture for 2 hours, separating the resulting methanol layer and distilling off low boiling fractions at 100° C./1 mmHg over one hour to obtain a colorless, transparent liquid (100 g) as a still residue (100 g). The results of $^1$H-NMR, IR spectra, hydroxyl group determination and gel permeation chromatography (GPC) of this product are described below and the product was confirmed to have the structure of the following formula:

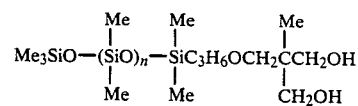

$^1$H—NMR (CDCl$_3$): δ (ppm)
  0.06(Si—Me$_3$, s, 420H)
  0.53(—CH$_2$—Si, m, 2H)
  0.83(CH$_3$—C≡, s, 3H)
  1.58(—CH$_2$—, m, 2H)
  3.10(C—OH, bs, 2H)
  3.37(—CH$_2$—, s, 2H)
  3.40(—CH$_2$—, s, 2H)
  3.63(—CH$_2$—, s, 4H)
IR (KBr) ν max
  3400 cm$^{-1}$ (O—H)
  2970 cm$^{-1}$ (C—H)
  1120~1050 cm$^{-1}$ (Si—O)

| | |
|---|---|
| Hydroxyl group | 0.60, |
| hence hydroxyl group equivalent | 2,800 |
| GPC: | |
| Number average molecular weight (Mn) as calculated based on polystyrene | 5,400 |
| Weight average molecular weight (Mw) as calculated based on polystyrene | 6,600 |
| Degree of dispersion (Mw/Mn) | 1.2 |

The following Examples are directed to those according to the present invention in the second aspect. "part" in these Examples means part by weight.

EXAMPLE 3

(1) 4,4'-Methylenebis(phenylisocyanate) (MDI) (5 parts) was added to a polyorganosiloxane expressed by the formula

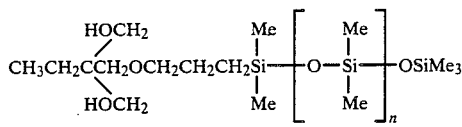

and having a molecular weight of about 1000 (n=9.5) (10 parts), followed by heating the mixture in 1,4-dioxane as solvent (35 parts by weight) at 80° C. for one hour.

(2) MDI (5 parts) was added to a polytetramethylene ether glycol (PTMG) having a molecular weight of about 2,000 (20 parts) in a reactor different from that used in the above paragraph (1), followed by heating the mixture in 1,4-dioxane as solvent (58 parts) at 80° C. for one hour.

(3) 1,4-Butanediol (3.8 parts) was added to a mixed solution of the solution of the above paragraph (1) (15 parts) with the solution of the above paragraph (2) (81 parts), followed by further adding 1,8-diazabicyclo[5,4,0]-7-undecene (D.B.U.) catalyst in 0.05% by weight based on MDT and reacting the mixture at 80° C. for one hour.

The resulting reaction solution was transferred into a large quantity of water, followed by depositing the resulting polymer, sufficiently washing it with water, drying and further washing with ethanol to obtain a silicone-modified polyrurethane of the present invention.

As to the mechanical properties of this polymer, the polymer was press-processed, and further a dumbbell was cut out, followed by measuring it using an autograph. Next, as to measurement of thrombosis resistance, the inner wall of a text tube having an inner diameter of 10 mm and a length of 100 mm was coated with a solution of the polymer dissolved in a mixed solvent of 1,4-dioxane/MEK (7/3) (solids concentration: 5%), followed by introducing fresh blood just after drawn (about 1 ml) and measuring the time at which the blood coagulated at 37° C. The results are shown in Table 1.

EXAMPLE 4

(1) 4,4'-Methylenebis(phenylisocyanate) (MDI) (one part) was added to a polyorganosiloxane expressed by the formula

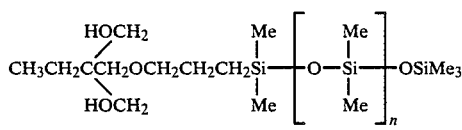

and having a molecular weight of about 5,000 (n=64.3) (10 parts), followed by heating the mixture in 1,4-dioxane as solvent at 80° C. for one hour.

(2) MDI (5 parts) was added to a polytetramethylene ether glycol (PTMG) having a molecular weight of about 2,000 (20 parts) in a reactor different from that of the above paragraph (1), followed by heating the mixture in 1,4-dioxane as solvent (58 parts) at 80° C. for one hour.

(3) 1,4-Butanediol (3.4 parts) was added to a mixed solution of the solution of the above paragraph (1) (5.5 parts) with the solution of the above paragraph (2) (91 parts), followed by further adding 1,8-diazabicyclo[5,4,0]-7-undecene (D.B.U.) as catalyst in 0.05% by weight based on MDI and heating the mixture at 80° C. for one hour.

The succeeding procedure was carried out in the same manner as in Example 3 to obtain a siliconemodified polyurethane of the present invention.

Further, the measurements of the mechanical properties of the polymer and the thrombosis resistance were carried out in the same manner as in Example 3. The results are shown in Table 1.

EXAMPLE 5

(1) 4,4'-methylenebis(phenylisocyanate)(MDI) (one part) was added to a polyorganosiloxane expressed by the formula

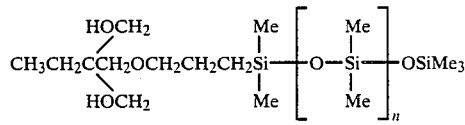

and having a molecular weight of about 5,000 (n=64.3) (10 parts) followed by heating the mixture in 1,4-dioxane as solvent (26 parts) at 80° C. for one hour.

(2) MDI (5 parts) was added to a polytetramethylene ether glycol (PTMG) having a molecular weight of about 2,000 (20 parts) in a reactor different from that of the above paragraph (1), followed by heating the mixture in 1,4-dioxane as solvent (58 parts) at 80° C. for one hour.

(3) 1,4-Butanediol (1.6 part) was added to a mixed solution of the solution of the above paragraph (1) (5.5parts) with the solution of the above paragraph (2) (43 parts), followed by further adding 1,8-diazabicyclo[5,4,0]-7-undecene (D.B.U.) as catalyst in 0.05% by weight based on MDI and heating the the mixture at 80° C. for one hour.

the succeeding procedure was carried out in the same manner as in Example 3 to obtain a silicone-modified polyurethane of the present invention.

Further, the measurements of the mechanical properties of the polymer and the thrombosis resistance were carried out in the same manner as in Example 3. The results are shown in Table 1.

EXAMPLE 6

(1) 4,4'-Methylenebis(phenylisocyanate) (MDI) (one part) was added to a polyorganosiloxane expressed by the formula

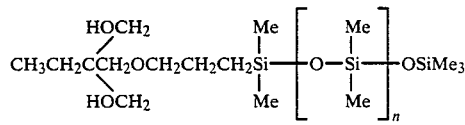

and having a molecular weight of about 5,000 (n=64.3) (10 parts), followed by heating the mixture in 1,4-dioxane as solvent at 80° C. for one hour.

(2) MDI (5 parts) was added to a polytetramethylene ether glycol (PTMG) having a molecular weight of about 2,000 (20 parts), followed by heating the mixture in 1,4-dioxane as solvent (58 parts) at 80° C. for one hour.

(3) 1,4-Butanediol (0.8 part) was added to a mixed solution of the solution of the above paragraph (1) (5.5 parts) with the solution of the above paragraph (2) (19 parts), followed by further adding 1,8-diazabicyclo-[5,4,0]-7-undecene (D.B.U.) as catalyst in 0.05% by weight based on MDI and heating the mixture at 80° C. for one hour.

the succeeding procedure was carried out in the same manner as in Example 3 to obtain a silicone-modified polyurethane of the present invention.

Further, the measurements of the mechanical properties of the polymer and the thrombosis resistance were carried out in the same manner as in Example 3. The results are shown in Table 1.

EXAMPLE 7

(1) 4,4'-Methylenebis(phenylisocyanate) (MDI) (one part) was added to a polyorganosiloxane expressed by the formula

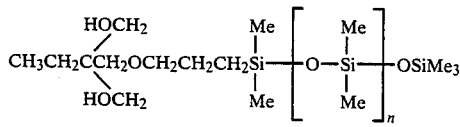

and having a molecular weight of about 10,000 ($n=132.8$) (20 parts), followed by heating the mixture in 1,4-dioxane as solvent (49 parts) at 80° C. for one hour.

(2) MDI (5 parts) was added to a polytetramethylene ether glycol (PTMG) having a molecular weight of about 2,000 (20 parts) in a reactor different from that used in the above paragraph (1), followed by heating the mixture in 1,4-dioxane as solvent (58 parts) at 80° C. for one hour.

(3) 1,4-Butanediol (3.2 parts) was added to a mixed solution of the solution of the above paragraph (1) (10.5 parts) with the solution of the above paragraph (2) (86.3 parts), followed by adding 1.8-diazabicyclo-[5,4,0]-7-undecene (D.B.U.) as catalyst in 0.05% by weight based on MDI and heating the mixture at 80° C. for one hour.

The succeeding procedure was carried out in the same manner as in Example 3 to obtain a silicone-modified polyurethane of the present invention.

Further, the measurements of the mechanical properties of the polymer and the thrombosis resistance were carried out in the same manner as in Example 3. The results are shown in Table 1.

COMPARATIVE EXAMPLE 1

(1) 4,4'-Methylenebis(phenylisocyanate) (MDI) (one part) was added to a polyorganosiloxane expressed by the formula

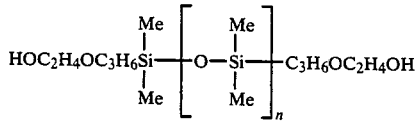

and having a molecular weight of about 5,000 ($n=64.9$) (10 parts), followed by heating the mixture in 1,4-dioxane as solvent (26 parts) at 80° C. for one hour.

(2) MDI (5 parts) was added to a polytetramethylene ether glycol (PTMG) having a molecular weight of about 2,000 (20 parts), followed by heating the mixture in 1,4-dioxane as solvent (58 parts) at 80° C. for one hour.

(3) 1,4-Butanediol (1.6 part) was added to a mixed solution of the solution of the above paragraph (1) (5.5 parts) with the solution of the above paragraph (2) (43 parts), followed by further adding 1,8-diazabicyclo-[5,4,0]-7-undecene as catalyst in 0.05% by weight based on MDI and heating the mixture at 80° C. for one hour.

The succeeding procedure was carried out in the same manner as in Example 3 to obtain a silicone-modified polyurethane.

Further, the measurements of the mechanical properties of the polymer and the thrombosis resistance were carried out in the same manner as in Example 3. The results are shown in Table 1.

COMPARATIVE EXAMPLE 2

(1) 4,4'-Methylenebis(phenylisocyanate) (MDI) (one part) was added to a polyorganosiloxane expressed by the formula

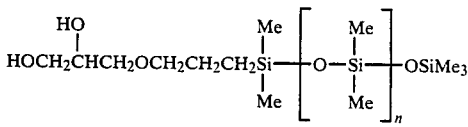

and having a molecular weight of about 5,000 ($n=64.7$) (10 parts), followed by heating the mixture in 1,4-dioxane as solvent (26 parts) at 80° C. for one hour.

(2) MDI (5 parts) was added to a polytetramethylene ether glycol (PTMG) having a molecular weight of about 2,000 (20 parts) in a reactor different from that used in the above paragraph (1),followed heating the mixture in 1,4-dioxane as solvent (58 parts) at 80° C. for one hour.

(3) 1,4-Butanediol (1.6 part) was added to a mixed solution of the solution of the above paragraph (1) (5.5 parts) with the solution of the above paragraph (2) (43 parts), followed by further adding 1,8-diazabicyclo-[5,4,0]-7-undecene (D.B.U.) in 0.05% by weight based on MDI and heating the mixture at 80° C. for one hour.

The succeeding procedure was carried out in the same manner as in Example 3 to obtain a silicone-modified polyurethane.

Further, the measurements of the mechanical properties of the polymer and the thrombosis resistance were carried out in the same manner as in Example 3. The results are shown in Table 1.

COMPARATIVE EXAMPLE 3

(1) MDI (5 parts) was added to a polytetramethylene ether glycol (PTMG) having a molecular weight of about 2,000 (20 parts), followed by heating the mixture in 1,4dioxane as solvent (58 parts) at 80° C. for one hour.

1,4-butanediol (0.9 part) was added to the solution of the above paragraph (1) (25 parts), followed by further adding 1,8 -diazabicyclo[5,4,0]-7-undecene (D.B.U.) as catalyst in 0.05% by weight based on MDI and heating the mixture at 80° C. for one hour.

The succeeding procedure was carried out in the same manner as in Example 3 to obtain a silicone-modified polyurethane.

Further, the measurements of the mechanical properties of the polymer and the thrombosis resistance were carried out in the same manner as in Example 3. the results are shown in Table 1.

TABLE 1

|  | Blood coagulation time (min.) LeeWhite | Mechanical properties | |
|---|---|---|---|
|  |  | Tensile strength (kg/cm$^2$) | Elongation (%) |
| Example 1 | 52 | 300 | 650 |
| Example 2 | 45 | 340 | 550 |
| Example 3 | 60 | 300 | 630 |
| Example 4 | 75 | 250 | 720 |
| Example 5 | 70 | 310 | 600 |
| Comp. ex. 1 | 37 | 230 | 750 |
| Comp. ex. 2 | 50 | 280 | 620 |
| Comp. ex. 3 | 17 | 380 | 500 |
| Test tube | 6 | — | — |

What we claim is:

1. A polysiloxane compound expressed by the formula

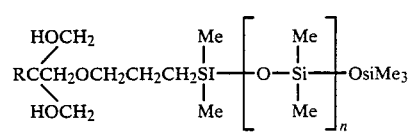

wherein R represents H, Me or Et, Me represents methyl group, Et represents ethyl group and n represents an integer of 0 to 4,000.

2. A polysiloxane compound according to claim 1 wherein said n represents an integer of 0 to 1,000.

* * * * *